United States Patent [19]

Smith et al.

[11] Patent Number: 5,240,712
[45] Date of Patent: Aug. 31, 1993

[54] THERAPEUTIC AGENTS

[75] Inventors: Alan Smith; John F. Lampard, both of Nottingham, England

[73] Assignee: The Boots Company PLC, England

[21] Appl. No.: 856,870

[22] Filed: Mar. 24, 1992

Related U.S. Application Data

[63] Continuation of Ser. No. 622,159, Nov. 30, 1990, abandoned.

[30] Foreign Application Priority Data

Jul. 17, 1987 [GB] United Kingdom ............... 8716975

[51] Int. Cl.$^5$ .............................................. A61K 31/74
[52] U.S. Cl. ................................... 424/451; 424/452; 424/474; 424/475; 424/476; 424/477; 424/478; 424/479; 424/480; 424/481; 424/482; 424/484; 424/485; 424/486; 424/487; 424/488; 514/570; 514/937; 514/938; 71/DIG. 1
[58] Field of Search .................. 424/78.1, 80, 83, 452, 424/451, 474–482, 484–488; 514/570, 937, 938; 71/DIG. 1

[56] References Cited

U.S. PATENT DOCUMENTS

| | | |
|---|---|---|
| 3,385,886 | 5/1968 | Nicholson et al. |
| 4,545,992 | 10/1985 | Kamishita ............................ 514/570 |
| 4,690,823 | 9/1987 | Lohner ................................ 514/570 |
| 4,786,495 | 11/1988 | Bird et al. ............................ 424/81 |
| 4,793,999 | 12/1988 | Seth .................................... 424/464 |

FOREIGN PATENT DOCUMENTS

| | | |
|---|---|---|
| 0172014 | 2/1986 | European Pat. Off. ............ 514/570 |
| 1617362 | 3/1983 | Fed. Rep. of Germany. |
| 0120616 | 9/1981 | Japan ................................... 514/570 |
| 1572226 | 3/1982 | United Kingdom. |

OTHER PUBLICATIONS

"Preparation and Dissolution Characteristics of Solid Dispersions of Ibuprofen . . . " by P. Mura et al., Il Farmaco, Jun. 1987, vol. XLII, No. 6, pp. 150–155.
"Phase Equilibria, Crystallinity and Dissolution Rates . . . " by Mura P. et al., Il Farmaco, Jun. 1987, vol. XLII, No. 6, pp. 157–164.

Primary Examiner—Lester L. Lee
Attorney, Agent, or Firm—Ostrolenk, Faber, Gerb & Soffen

[57] ABSTRACT

A high content of 2-(4-isobutylphenyl)propionic acid is achieved in a pharmaceutical composition by solidifying molten 2-(4-isobutylphenyl)propionic acid to provide a unit dose composition. The composition may be prepared by heating the 2-(4-isobutylphenyl)-propionic acid until molten, optionally mixing with pharmaceutically acceptable excipients, forming into a unit dosage presentation and allowing the composition to solidify. Preferably the composition contains greater than 80% ibuprofen or S(+)-ibuprofen and is filled into a hard gelatin capsule.

12 Claims, No Drawings

THERAPEUTIC AGENTS

This is a continuation of application Ser. No. 07/622,159 filed on Nov. 30, 1990 and now abandoned.

This invention relates to therapeutic agents, and in particular to pharmaceutical compositions containing 2-(4-isobutylphenyl)propionic acid, in particular ibuprofen.

Ibuprofen is (+)2-(4-isobutylphenyl)propionic acid. It is a potent and well tolerated peripherally acting analgesic, anti-inflammatory and anti-pyretic compound. The racemic mixture representing ibuprofen, may be resolved into two enantiomers, namely S(+)-ibuprofen and R(-)-ibuprofen.

Japanese Patent Application 120616 discloses formulations containing granules of ibuprofen. The granules are formed by heating the ibuprofen until molten, optionally adding excipients, cooling to form a solid melt and then crushing the melt to form granules. The granules may then be mixed with excipients using conventional techniques and formulated into a solid dosage form, e.g. by compression to form a tablet.

It has now been found however that formulation advantages are obtained when 2-(4-isobutylphenyl)-propionic acid is melted and formed into a unit dosage form before allowing to solidify.

Accordingly the present invention provides a unit dose pharmaceutical composition comprising 2-(4-isobutylphenyl)propionic acid optionally together with excipients, wherein the composition is formed as a fused 2-(4-isobutylphenyl)propionic acid unit dose composition.

The unit dose pharmaceutical composition may consist of 2-(4-isobutylphenyl)propionic acid optionally together with excipients, solidified from the molten state. Thus, a composition according to the invention may be prepared by melting 2-(4-isobutylphenyl)propionic acid optionally together with excipients, forming the molten mass into a unit dosage form and causing the molten mass to solidify. Accordingly, in another aspect the invention provides a pharmaceutical composition comprising 2-(4-isobutylphenyl)propionic acid which has been melted, formed into a unit dosage form and allowed to solidify. The unit dose composition may consist of a solidified melt of 2-(4-isobutylphenyl)propionic acid optionally together with excipients. The composition may be a fused matrix of 2-(4-isobutylphenyl)propionic acid, optionally containing excipients.

It will be appreciated that the term 2-(4-isobutylphenyl)propionic acid includes the racemic mixture and the S(+)- and R(-)-enantiomers separately.

It has been found that the release characteristics of the composition can be varied over a wide range by means of the incorporation of other excipients. A further advantage lies in the high proportions of 2-(4-isobutylphenyl)propionic acid in the dosage form. In addition, the composition may easily be prepared to provide stable formulations.

The form of the 2-(4-isobutylphenyl)propionic acid in the compositions of this invention is a fused unit dose composition. The material is distinct from granulated, powdered or micronised material and does not contain discrete particles. The 2-(4-isobutylphenyl)propionic acid composition is preferably formed by moulding. The composition has satisfactory crushing strength, with preferred compositions having a crushing strength from 5-10 kp.

In one embodiment, the composition of the invention also comprises at least one pharmaceutically acceptable excipient. In order to be incorporated into the solidified composition, the excipient or excipients are most conveniently mixed with the 2-(4-isobutylphenyl)propionic acid whilst the latter is in the molten state. Those excipients which are soluble in the molten 2-(4-isobutylphenyl)propionic acid form a solid solution or dispersion when solidified, whereas excipients which are insoluble in molten 2-(4-isobutylphenyl)propionic acid provide a solid dispersion. When more than one excipient is employed, it is possible, for example, that one or more excipients may dissolve in the molten 2-(4-isobutylphenyl)propionic acid and others may be insoluble, so that on solidification, a mixture of a solid solution and a solid dispersion results.

Accordingly in a further aspect, this invention provides a pharmaceutical composition in unit dosage form consisting of a solid solution and/or dispersion of at least one pharmaceutically acceptable excipient in 2-(4-isobutylphenyl)propionic acid.

When the 2-(4-isobutylphenyl)propionic acid optionally together with the excipients, is solidified from the molten state, it may be formed into any desired solid dosage presentation, for example soft and hard gelatin capsules, tablets, lozenges, pastilles, suppositories or implants. Generally, though not exclusively, these compositions may be formed by allowing the molten 2-(4-isobutylphenyl)propionic acid to solidify in a shaped mould.

A preferred dosage form is a hard gelatin capsule. The molten 2-(4-isobutylphenyl)propionic acid can be pumped readily and may be filled, on a suitable capsule-filling machine, into hard gelatine capsules, where it solidifies on cooling.

The unit dosage composition of this invention may consist essentially of 2-(4-isobutylphenyl)propionic acid alone filled, for example, into hard gelatin capsules. That composition has been found to have sustained release properties and the dissolution rate thereof is significantly greater than capsules containing the equivalent amount of powdered 2-(4-isobutylphenyl)propionic acid. However it is a further aspect of this invention that the release characteristics of the composition can be varied over a wide range by the incorporation of one or more excipients. This is a particularly advantageous feature as it allows the release rate to be modified as desired to provide a carefully controlled dissolution rate. It is not necessary that the release modifying excipient forms a substantial proportion of the composition, accordingly by making minor changes in the choice of excipients in the composition, significant differences in release rates may be obtained whilst maintaining a high level of 2-(4-isobutylphenyl)propionic acid. The formulation may be adapted to provide sustained release of 2-(4-isobutylphenyl)propionic acid. Alternatively excipients may be added to disperse the composition on ingestion into the body thus making the 2-(4-isobutylphenyl)propionic acid immediately available for absorption. Also by careful selection of pharmaceutical excipients, any intermediate release rate may be achieved.

Suitable pharmaceutically acceptable excipients which produce a retarded rate of dissolution include both hydrophilic and hydrophobic excipients such as the following, or mixtures thereof: beeswax, stearic acid, palmitic acid, myristic acid, lauric acid, stearyl alcohol, cetyl alcohol, glyceryl stearate, ethyl oleate, arachis oil, cotton seed oil, rape seed oil, liquid paraffin, polyethylene glycols, in particular grades 400, 4000, 6000 and 20000; colloidal silicon dioxide, such as Aerosil (trade mark) for example grades 200 and R972, mono-, di- and/or triglycerides such as Miglyol 812 (trade mark), Labrafil (trade mark), Precirol (trade mark), in particular grade A205, and Gelucire, in particular grades 62/05, 50/13, 46/07, 44/14, 35/10 and 37/02.

Suitable pharmaceutically acceptable excipients which produce an accelerated rate of dissolution are generally disintegrants such as the following, or mixtures thereof:

rice starch, potato starch, wheat starch, maize starch, other vegetable starches, modified starch and starch derivatives: cellulose, cellulose derivatives and modified cellulose derivatives for example methylcellulose, hydroxypropylmethylcellulose, and substituted hydroxypropylcellulose; alginic acid and alginates; bentonite, ion exchange resins, gums, surfactants, sodium croscarmellose (AcDisol - trade mark), sodium starch glycollate (Explotab - trade mark) cross-linked polyvinylpyrrolidones such as Kollidon XL (trade mark).

Other pharmaceutically acceptable excipients which may be used to aid or further accelerate dissolution are surfactants, emulsifiers, solubilising agents and pH modifying agents, e.g. bases and buffering agents.

Preferred disintegrant excipients include maize starch, sodium croscarmellose, and sodium starch glycollate.

Mixtures of retardant and accelerant excipients can employed to produce a composition within this invention having the desired release characteristics. Surprisingly low levels of excipients can be incorporated into the molten 2-(4-isobutylphenyl) -propionic acid to produce significant differences in release characteristics in the compositions of this invention. The quantity of excipient employed depends on the release characteristics required and the nature of the excipient. For a sustained release composition the level of excipients, which may include at least one retardant or dissolution aid as exemplified above, is suitably up to 20%, i.e. 0 to 20%, advantageously up to 10%, i.e. 0–10%, by weight of the total composition, for example from zero to 2.5%. Preferably the level of excipients is from 2–8% by weight, especially from 2–5, % by weight. For a more rapid release of 2-(4-isobutylphenyl)propionic acid from the composition, an excipient or mixture of excipients is employed which contain at least one excipient producing an accelerated rate of dissolution as exemplified above. For the more potent disintegrants, such as sodium croscarmellose, and sodium starch glycollate, a low level of excipient may be used, for example from 0.1 to 10%, especially from 2–5% by weight of the composition. For less potent disintegrants such as starches and alginic acid, higher levels should be used, for example from 2.5–50% by weight, preferably at least 5%, e.g. 5–25% by weight, and especially from 10–20% by weight. It will be appreciated that upper levels of solid insoluble excipients are limited by the fact that the molten 2-(4-isobutylphenyl)propionic acid system must be of sufficiently low viscosity to be handled accurately, for example by a capsule filling machine.

There may also be incorporated into the compositions of the present invention additional pharmaceutically acceptable non-toxic ingredients recognised in the art of pharmaceutical formulation such as binders, for example pregelled starches, microcrystalline cellulose, gelatine, gums; soluble diluents, for example lactose, sodium chloride, dextrins, sorbitol lubricants for example magnesium stearate; flow aids such as talc and other oils, fats and waxes.

Each unit dose composition suitably contains from 50 to 1500 mg of 2-(4-isobutylphenyl) propionic acid preferably from 200 to 1300 mg, particularly 200 to 80 mg. The dosage as employed for an adult human treatment is suitably in the range from 100 to 3000 mg per day.

The amount of 2-(4-isobutylphenyl)propionic acid present in the composition is sufficient to for a fused matrix, for example from 50 to 100% by weight ibuprofen. However, a particular advantage of the compositions of this invention is that high levels of 2-(4-isobutylphenyl)propionic acid can be employed. Thus the present compositions preferably comprise at least 80% by weight of 2-(4-isobutylphenyl)propionic acid, for example 80–100%, more preferably 90%–99%, especially at least 95%, for example 95–97% by weight. Preferred compositions may contain 90–100% by weight 2-(4-isobutylphenyl)propionic acid and 0–10% by weight disintegrant, especially 94–99% by weight 2-(4-isobutylphenyl)propionic acid and 1–6% by weight disintegrant. Such high proportions of 2-(4-isobutylphenyl)propionic acid in the composition are particularly valuable for high dose formulations. Accordingly, preferably the ratio of 2-(4-isobutylphenyl)propionic acid to excipients is in the range 100:1–10:1, especially 50:1–20:1 by weight.

In particular the provisions of a high dose composition having sustained release properties enables a unit dosage composition of 2-(4-isobutylphenyl) -propionic acid to be produced which is suitable for once- or twice-a-day administration, preferably once-a-day. Such compositions will suitably comprise from 400 to 1300 mg, preferably from 600 to 800 mg of 2-(4-isobutylphenyl)-propionic acid.

In an especially preferred aspect the unit dosage forms of the present invention include ibuprofen and S(+)-ibuprofen. S(+)-ibuprofen has particularly advantageous processing, formulation and therapeutic properties.

Compositions of the present invention are of particular value in the treatment of pain and inflamation, including rheumatoid arthritis and osteoarthritis.

The compositions of this invention may be prepared by a process which comprises heating 2-(4-isobutylphenyl)propionic acid, optionally together with at least one pharmaceutically acceptable excipient until molten, and forming into a unit dosage form, for example by moulding, wherein the 2-(4-isobutylphenyl)propionic acid solidifies. When the dosage form is a hard gelatin capsule, the following procedure is conveniently carried out.

2-(4-Isobutylphenyl)propionic acid together with other meltable ingredients, if required, is placed in a suitable vessel and warmed with stirring until molten. To the molten mass, any required liquid, soluble or dispersible solid ingredients are added with stirring to give a homogeneous mass. This mass is brought to a temperature of 70°–80° C. and filled volumetrically into the body of a suitably sized hard gelatin capsule, which is then closed by the fitting and locking of the cap.

It is a particular feature of the present invention that the viscosity of the composition may be readily modified. This is an important aspect when it is desired to pump the molten composition into a capsule, for example a hard gelatin capsule, as the viscosity of a material is an important processing factor. Other parameters affecting the processing of the composition will be the temperature of the melt, the cooling rate and the stirring time and stirring rate. The variables will vary from one formulation to the next and the individual parameters necessary will be readily appreciated by a man skilled in the art.

The preparation of compositions of the present invention is illustrated by the following Examples. The dissolution rate was measured using the apparatus described in U.S. Pharmacopoeia XX, apparatus II, with 900 ml of pH 7.2 buffer and a paddle speed of 50 rev.min$^{-1}$, measuring the content of ibuprofen spectrophotometrically at suitable intervals. The dissoltion rates are expressed as follows:

$T_{50}$: time taken for 50% of the ibuprofen to dissolve:
$T_{90}$: time taken for 90% of the ibuprofen to dissolve.

In the Examples, colloidal silicon dioxide is available from Degussa, Frankfurt, Germany under the trade name Aerosil; croscarmellose sodium is available from FMC, Philadelphia, USA, under the trade name Ac-DiSol: the glyceride material is available from Gattefosse, France under the trade name Gelucire 50/13; and sodium starch glycollate is available from Edward Mendell Corporation, Carmel, USA, under the trade name Explotab: the polyoxyethylene-polyoxypropylene block copolymer is available from BASF (UK) Ltd, Cheshire, UK, under the trade name Pluronic F68.

EXAMPLE 1

A formulation containing per size 0 capsule

| ibuprofen | 600 mg |
|---|---|
| stearyl alcohol | 6.0 mg | was prepared by warming ibuprofen and stearyl alcohol together with stirring to form a homogeneous molten mass. This mass was brought to a temperature of about 75° C. and then filled volumetrically by pipette into the capsule. The mass was allowed to cool before presentation as a unit dose. Measurement of the dissolution of ibuprofen from these capsules gave $T_5$ 10 hours and $T_{90}$ >24 hours.

EXAMPLE 2

A formulation containing per elongated size 0 capsule

| ibuprofen | 600 mg |
|---|---|
| polyethylene glycol 4000 | 60 mg | was prepared and filled as in Example 1 and gave capsules with a dissolution $T_{50}$ of 3.3 hours and $T_{90}$ of 6.8 hours.

EXAMPLE 3

A formulation containing per elongated size 0 capsule

| ibuprofen | 600 mg |
|---|---|
| maize starch | 30 mg | was prepared by warming the ibuprofen until molten then adding the maize starch gradually with stirring to form a homogeneous molten suspension. This suspension was transferred to a heated stirred reservoir feeding a volumetric pump and capsules were filled via the pump. The mass was allowed to cool before presentation as a unit dose. Capsules of this formulation gave $T_{50}$ of 1.6 hours and $T_{90}$ of 4.6 hours when dissolution tested.

EXAMPLE 4

A capsule size 00 formulated to contain

| ibuprofen | 800 mg |
|---|---|
| Aerosil R972 | 8 mg |
| Beeswax | 8 mg | was prepared by melting the ibuprofen and beeswax together and adding the Aerosil R972 (trade mark) with stirring to form a homogeneous suspension. Capsules were filled as in Example 3 and gave the following dissolution value: $T_{50}$ 15 hours.

EXAMPLE 5

| ibuprofen | 600 mg |
|---|---|
| Acdisol (trade mark) | 30 mg |
| Aerosil 200 (trade mark) | 18 mg | was produced by the addition with stirring of the Aerosil followed by the Acdisol. Capsules were hand filled by pipette with this molten suspension. The mass was allowed to cool before presentation as a unit dose. Measurement of the dissolution of ibuprofen from these capsules gave $T_{50}$ 0/7 hours and $T_{90}$ 2.8 hours.

EXAMPLE 6

A formulation containing per size 1 capsule

| ibuprofen | 400 mg |
|---|---|
| Acdisol | 10 mg | was prepared and filled into capsules according to the method of Example 3. Measurement of dissolution of ibuprofen gave a $T_{50}$ of <20 minutes.

EXAMPLE 7

The maximum ibuprofen fill weight of alternative capsule sizes was found to be as shown in Table 1.

TABLE 1

| Capsule Size | Approximate Fill (mg) |
|---|---|
| 1 | 450 |
| 0 | 605 |
| 0 (elongated) | 680 |
| 00 | 825 |

EXAMPLE 8

Table 2 indicates the dissolution data for a range of ibuprofen 600 mg formulations prepared as described in a similar manner as described in any one of Examples 1-6.

TABLE 2

| Excipient | Amount of ibuprofen (% w/w) | Amount of Excipient (% w/w) | $T_{50}$ (hours) |
|---|---|---|---|
| None | 100 | — | 2.9 |
| Arachis Oil | 90 | 10 | 4.1 |
| Beeswax | 90 | 10 | >24 |

TABLE 2-continued

| Excipient | Amount of ibuprofen (% w/w) | Amount of Excipient (% w/w) | $T_{50}$ (hours) |
|---|---|---|---|
| Beeswax | 90* | 10 | 9.5 |
| Colloidal Silicon Dioxide (Aerosil 200) | 99 | 1 | 4.7 |
|  | 97 | 3 | 6.6 |
|  | 95 | 5 | 10.0 |
| Colloidal Silicon Dioxide (Aerosil R972) | 99 | 1 | 5.9 |
|  | 95 | 5 | 20.5 |
| Croscarmellose sodium (AcDiSol) | 99 | 1 | 0.4 |
|  | 97.5 | 2.5 | 0.13 |
| Glycerides (Gelucire 50/13) | 95 | 5 | 3.0 |
| (Gelucire 50/13) | 90 | 10 | 7.4 |
| (Gelucire 50/13) | 90* | 10 | 2.9 |
| Liquid Paraffin | 90 | 10 | 4.8 |
| Maize Starch | 99 | 1 | 3.5 |
| Copolymer (Pluronic F68) | 95 | 5 | 1.6 |
|  | 90 | 10 | 0.16 |
|  | 95 | 5 | 3.0 |
| Polyethylene glycol - |  |  |  |
| i) molecular weight 400 | 90 | 10 | 3.5 |
| ii) molecular weight 4000 | 90 | 10 | 3.3 |
| iii) molecular weight 6000 | 90 | 10 | 4.2 |
| Polyvinylpyrrolidone (Crosprovidone) | 90 | 10 | 4.0 |
| Sodium starch glycollate (Explotab) | 99 | 1 | 1.8 |
|  | 95 | 5 | 0.3 |
| Stearic Acid | 99 | 1 | 4.2 |
|  | 95 | 5 | 7.8 |
|  | 90 | 10 | >24 |
| Stearyl Alcohol | 99 | 1 | 10.0 |
|  | 95 | 5 | 14.0 |
|  | 90 | 10 | >24 |

Note:
*indicates S(+)-ibuprofen

EXAMPLE 9

Table 3 indicates the dissolution data for a range of ibuprofen 400 mg formulations prepared in a similar manner as described in any one of Examples 1–6.

TABLE 3

| Excipient | Amount of Ibuprofen (% w/w) | Amount of Excipient (% w/w) | $T_{50}$ (hours) |
|---|---|---|---|
| None | 100 | — | 2.2 |
| None | 100* | — | 3.0 |
| None | 100** | — | 3.8 |
| Stearyl alcohol | 95 | 5 | 10.0 |
| Stearyl alcohol | 95* | 5 | 2.0 |
| Stearyl alcohol | 99* | 1 | 2.6 |
| Stearyl alcohol | 95** | 5 | 2.1 |
| Croscarmellose | 97.5 | 2.5 | 0.22 |

TABLE 3-continued

| Excipient | Amount of Ibuprofen (% w/w) | Amount of Excipient (% w/w) | $T_{50}$ (hours) |
|---|---|---|---|
| Sodium (AcDiSol) | 97.5* | 2.5 | 0.16 |

Note:
*indicates S(+)-ibuprofen
** indicates R(−)-ibuprofen

EXAMPLE 10

Table 4 indicates the variation in dissolution rates obtained by using different proportions of colloidal silicon dioxide in relation to other excipients in compositions containing 600 mg ibuprofen. The formulations were prepared in a similar manner as described in any one of Examples 1–6.

TABLE 4

| Colloidal Silicon Dioxide | Further Excipient | Amount of Ibuprofen (% w/w) | Amount of Colloidal Silicon Dioxide (% w/w) | Amount of Further Excipient (% w/w) | $T_{50}$ (hour) |
|---|---|---|---|---|---|
| Aerosil 200 | Croscarmellose Sodium (AcDisol) | 98 | 1 | 1 | 1.0 |
| Aerosil 200 | Croscarmellose Sodium (AcDisol) | 96 | 3 | 1 | 6.0 |
| Aerosil 200 | Croscarmellose Sodium (AcDisol) | 92 | 3 | 5 | 0.7 |
| Aerosil 200 | Croscarmellose Sodium (AcDisol) | 94 | 1 | 5 | 0.3 |
| Aerosil 200 | Stearic Acid | 98 | 1 | 1 | 11.7 |
| Aerosil R972 | Stearic Acid | 98 | 1 | 1 | 9.8 |
| Aerosil R972 | Stearyl Alcohol | 98 | 1 | 1 | 15.0 |
| Aerosil R972 | Beeswax | 98 | 1 | 1 | 15.0 |

EXAMPLE 11

Table 5 shows the variation on viscosity measurements achieved by the use of excipients in 600 mg ibuprofen compositions. The viscosity was measured using a Contraves Rheomat 15 apparatus at 70° C.

TABLE 5

| Excipient | Amount of Ibuprofen (% w/w) | Amount of Excipient (% w/w) | Viscoscity (cp) |
|---|---|---|---|
| None | 100 | — | 27 |
| Beeswax | 95 | 5 | 27 |
| Colloidal silicon dioxide |  |  |  |
| Aerosil 200 | 99 | 1 | 28 |
| Aerosil 200 | 98 | 2 | 35 |
| Aerosil 200 | 97 | 3 | 60 |
| Aerosil 200 | 96 | 4 | 1258 |
| Aerosil 200 | 95 | 5 | 2123 |
| Aerosil R972 | 96 | 4 | 900 |

EXAMPLE 12

A formulation containing

| | |
|---|---|
| S(+)-ibuprofen | 300 mg |
| polyethylene glycol 6000 | 100 mg |
| maize starch | 100 mg | was prepared by warming S(+)-ibuprofen and polyethylene glycol until molten and then adding the maize starch gradually with stirring to form a homogenous molten suspension. The mixture was poured into a mould and allowed to cool to form a solid plug of material.

EXAMPLE 13

A formulation containing per size 00 capsule

| S(+)-ibuprofen | 600 mg |
|---|---|
| hydrogenated rape seed oil | 200 mg | was prepared by warming S(+)-ibuprofen and the rape seed oil together with stirring to form a homogenous molten mass. This mass was bought to a temperature of about 60° C. and then dispensed into the capsule. The mass was allowed to cool before presentation as a unit dose.

EXAMPLE 14

A formulation containing per size 0 (elongated) capsule

| ibuprofen | 400 mg |
|---|---|
| polyethylene glycol | 100 mg | was prepared by warming ibuprofen and polyethylene glycol together with stirring at 75°-80° C. to form a homogenous molten mass. This mass was dispensed into the capsule. The mass was allowed to cool before presentation as a unit dose.

EXAMPLE 15

A formulation containing per size 00 capsule

| ibuprofen | 600 mg |
|---|---|
| maize starch | 100 mg | was prepared by heating the ibuprofen until molten and then adding the maize starch gradually with stirring at 80° C. to form a homogenous molten suspension. The suspension was dispensed into a capsule. The mass was allowed to cool before presentation as a unit dose.

We claim:

1. A solid sustained release unit dose pharmaceutical composition useful for treating pain, inflammation and fever in humans and animals which comprises a therapeutically effective amount of 2-(4-isobutylphenyl)propionic acid, said composition containing 80% to 100% by weight 2-(4-isobutylphenyl)propionic acid and being in the form of a fused matrix of 2-4-isobutylphenyl)propionic acid which has been melted, formed into unit dosage form and allowed to solidify and which may contain one or more excipients as a solid solution and/or dispersion of said excipient or excipients in 2-(4-isobutylphenyl)propionic acid.

2. A composition according to claim 1 wherein the composition comprises 90-100% by weight 2-(4-isobutylphenyl)propionic acid and 0-10% by weight disintegrant.

3. A composition according to claim 1 in which the composition comprises at least 95% by weight 2(4-isobutylphenyl)propionic acid.

4. A composition according to claim 1 comprising ibuprofen or S(+)-ibuprofen.

5. A composition according to claim 1 contained in a gelatin capsule.

6. A composition according to claim 1 comprising one or more of the following: polyethylene glycol, maize starch, colloidal silicon dioxide, beeswax, croscarmellose sodium, arachis oil, glycerides, liquid paraffin, polyvinylpyrrolidone, sodium starch glycollate, stearic acid, stearyl alcohol, mono- and/or di- and/or triglycerides, hydrogenated rape seed oil, or polyoxyethylene-polyoxypropylene block copolymer.

7. A sustained release pharmaceutical composition in unit dosage form useful for treating pain, inflammation and fever in humans and animals which comprises a therapeutically effective amount of 2-(4-isobutylphenyl)propionic acid, said 2-(4-isobutylphenyl)propionic acid being present in an amount of 80% to 100 by weight of the composition in the form of a fused matrix of 2-(4-isobutylphenyl) propionic acid which has been solidified as said unit dose from the molten state and said composition consisting of a solid solution and/or dispersion of at least one pharmaceutically acceptable excipient in 2-(4-isobutylphenyl) propionic acid.

8. A solidified non-comminuted sustained release unit dose pharmaceutical composition comprising 50 to 1500 milligrams of 2-(4-isobutylphenyl)propionic acid and up to about 20 weight % (based on he total weight) of at least one pharmaceutically acceptable excipient therefor wherein the 2-(4-isobutylphenyl)propionic acid has been melted, formed into unit dose form and allowed to solidify into a fused matrix.

9. The solidified unit dose composition of claim 8 of 200 to 1300 milligrams of 2(4-isobutylphenyl)propionic acid and up to 10 weight % excipient and having a crushing strength of 5 to 10 kp.

10. The solidified unit dose composition of claim 9 containing 200 to 800 milligrams of 2(4-isobutylphenyl)-propionic acids.

11. The solidified unit dose composition of claim 10 containing 2 to 5 weight % excipient.

12. A solidified non-comminuted sustained release unit dose pharmaceutical composition of claim 11 which has a crushing strength of 5 to 10 kp and consists of 200 to 800 milligrams of S(+)-2(4-isobutylphenyl)-propionic acid and 2 to 5 weight % (based on the total weight) of at least one pharmaceutically acceptable excipient therefor wherein the 2-(4-isobutylphenyl)pripionic acid has been melted, formed into unit dose form and allowed to solidify into a fused matrix.

* * * * *